United States Patent [19]
Eadie et al.

[11] Patent Number: 5,445,933
[45] Date of Patent: * Aug. 29, 1995

[54] STRAND DISPLACEMENT ASSAY AND COMPLEX USEFUL THEREFOR

[75] Inventors: James S. Eadie, Indianapolis; Neil G. Balgobin, Carmel, both of Ind.; Harvey Buck, Weilheim, Germany

[73] Assignee: Boehringer Mannheim Corporation, Indianapolis, Ind.

[*] Notice: The portion of the term of this patent subsequent to Feb. 14, 2012 has been disclaimed.

[21] Appl. No.: 945,156

[22] Filed: Sep. 15, 1992

[51] Int. Cl.⁶ .............................................. C12Q 1/68
[52] U.S. Cl. ...................... 435/6; 536/24.32
[58] Field of Search ................. 435/6; 536/24.3, 24.32

[56] References Cited

U.S. PATENT DOCUMENTS

| | | | |
|---|---|---|---|
| 4,725,536 | 2/1988 | Fritsch et al. | 435/6 |
| 4,725,537 | 2/1988 | Fritsch et al. | 435/6 |
| 4,735,897 | 4/1988 | Vary et al. | 435/6 |
| 4,752,566 | 6/1988 | Collins et al. | 435/6 |
| 4,766,062 | 8/1988 | Diamond et al. | 435/810 |
| 4,766,064 | 8/1988 | Williams et al. | 435/810 |
| 4,767,699 | 8/1988 | Vary et al. | 435/6 |
| 4,795,701 | 1/1989 | Vary | 435/6 |
| 4,818,680 | 4/1989 | Collins et al. | 435/6 |

OTHER PUBLICATIONS

Sambrook et al., Molecular Cloning, Cold Spring Harbor Laboratory, New York, 1989, pp. 11.45–11.47, 11.55–11.57.

Heller et al. DNA Probes (Stockton Press, 1989), pp. 195–198.

Primary Examiner—Margaret Parr
Assistant Examiner—Scott W. Houtteman
Attorney, Agent, or Firm—Felfe & Lynch

[57] ABSTRACT

The invention relates to an improvement in the strand displacement assay. Probes that are at least 20 nucleotide bases in length, but are no more than 40 bases in length, are used. These short probes permit detection and discrimination down to the order of a single base.

7 Claims, 18 Drawing Sheets

STRAND DISPLACEMENT ASSAY AND COMPLEX USEFUL THEREFOR

FIELD OF THE INVENTION

This invention relates to the field of clinical analysis. More specifically, it relates to analytical methods and apparatus which utilize improvements on the well known strand displacement assay. Additionally, the invention relates to nucleic acid sequences which are useful in assays for *Neisseria gonorrhoeae* using the strand displacement assay methodology, as well as in other nucleic acid probe assays.

BACKGROUND AND PRIOR ART

One family of diagnostic assays that has become well known and accepted in the field of clinical chemistry is based upon nucleic acid hybridization. It is well known that nucleic acid molecules (DNA and RNA) can and do hybridize to complementary strands of nucleic acids, thereby forming double stranded molecules.

The principles of nucleic acid hybridization is built upon two deceptively simple rules. All nucleic acid molecules consist of four nucleotide bases DNA contains bases "A", "T", "C" and "G", whereas RNA contains "A", "U", "C" and "G". The two simple rules referred to supra are (i) the bases "A" and "T" and "U" complement and hybridize to each other, and "C" and "G" to each other. Nucleic acid molecules of varied and great lengths can be formed via the binding of bases to each other.

The ability to identify particular organisms, viruses, mutations in DNA/RNA sequences, etc., relies on the presence of sequences unique to the material to be identified, and the hybridization principles referred to supra. For example, if microorganism "X" contains unique DNA sequence:

5'-AAACCGGCC-3' it is theoretically possible to identify the microorganism by making the unique sequence accessible and contacting it by its complement:

3'-TTTGGCCGG-5

If the complement contains a label, i.e., some "marker" it will be possible to note that hybridization has occurred. It is this principle that is the core of all nucleic acid determination assays.

The strand displacement assay is generally described in a series of U.S. Patents, i.e. U.S. Pat. Nos. 4,629,689 (Diamond et al.), 4,725,536 (Fritsch et al.), 4,725,537 (Fritsch et al.), 4,735,897 (Vary et al.), 4,752,566 (Collins et al.), 4,766,062 (Diamond et al.), 4,766,064 (Williams et al.), 4,767,699 (Vary et al.), 4,795,701 (Vary), 4,818,680 (Collins et al.). Essentially, it involves the contacting of a test sample believed to contain a nucleic acid sequence of interests with a hybrid complex of two nucleic acid sequences of differing lengths. The longer sequence is referred to as the binding probe, and is complementary to the nucleic acid sequence of interest. A shorter sequence, referred to as the signal probe, is hybridized to only a portion of the binding probe. That portion of the binding probe which is not hybridized to signal probe is referred to as the initial binding region. For example, using the sequence example given supra:

5'-AAACCGGCC-3' a hybrid complex such as the following may be prepared:

TTGGCCGG

GGCC wherein "TTGGCCGG" is the binding probe, "TTGG" is the initial binding region, and "GGCC" is the signal probe. In practice, the binding probe binds to the target sequence via the initial binding region, or "IBR". The binding probe continues to hybridize to the target molecule, because it is longer than the signal probe, and complexes which include longer molecules are more stable. Nucleic acids do not form stable triplex complexes, however, and thus the signal probe is "displaced". When the signal probe is labelled, this displacement can be measured.

The strand displacement assay is useful, but is not without its problems, not the least of which is sensitivity. Pathological conditions are known, e.g., where a difference between normality and abnormality rests in a single nucleotide base difference. Sickle cell anemia is simply the most well known example of a pathological condition identified by this type of point mutation. There are other analytes where determination of a single nucleotide base is important, or where differences between various microorganisms is slight. Identification and determination in such contexts requires levels of sensitivity and specificity not previously obtainable with strand displacement assays.

One organism which has been studied quite extensively in connection with nucleic acid assays is *Neisseria gonorrhoeae*, the causative agent of a sexually transmitted disease, with an estimated two million reported cases per year. Examples of the patent literature regarding *N. gonorrhoeae* specific nucleic acid probes include U.S. Pat. Nos. 4,900,659 to Lo et al, and 5,047,523 and 5,099,011 both to Woods et al. These patents deal with DNA:DNA hybridization, and disclose probes which, while useful, are simply not very specific.

Additionally, published patent applications WO90/14442, EPA 337,896, EPA 272009 and EPA 408077 disclose hybridization between RNA and complementary probes. These patents represent developments on the patent of Kohne, U.S. Pat. No. 4,851,330, which identified organisms by detecting unique RNA sequences, in that the rRNA sequence of the organism is the target.

None of these references teach the specific nucleic acid probes for *N. gonorrhoeae*, disclosed herein, which are useful in various diagnostic assays including the strand displacement assay. Not only are the sequences disclosed herein unique, they function as specific *N. gonorrhoeae* probes. With respect to this statement, it must be pointed out that uniqueness of a specific sequence does not necessarily mean that the sequence will function as a probe. Various considerations, including the total length of the probe, the ability to identify large numbers of strains of the organism, micro heterogeneity, etcetera must be considered.

In view of the difficulty of identifying probes which are useful as *N. gonorrhoeae* probes, it is surprising that probes which vary in only a single base pair from comparable sequences of different species of Neisseria can be used to identify *N. gonorrhoeae*. Such probes are another feature of the invention as described herein.

BRIEF DESCRIPTION OF THE FIGURES

FIG. 6 demonstrates the sensitivity of the assay.

DETAILED DESCRIPTION OF THE PREFERRED EMBODIMENTS

Example 1

Figure 1:
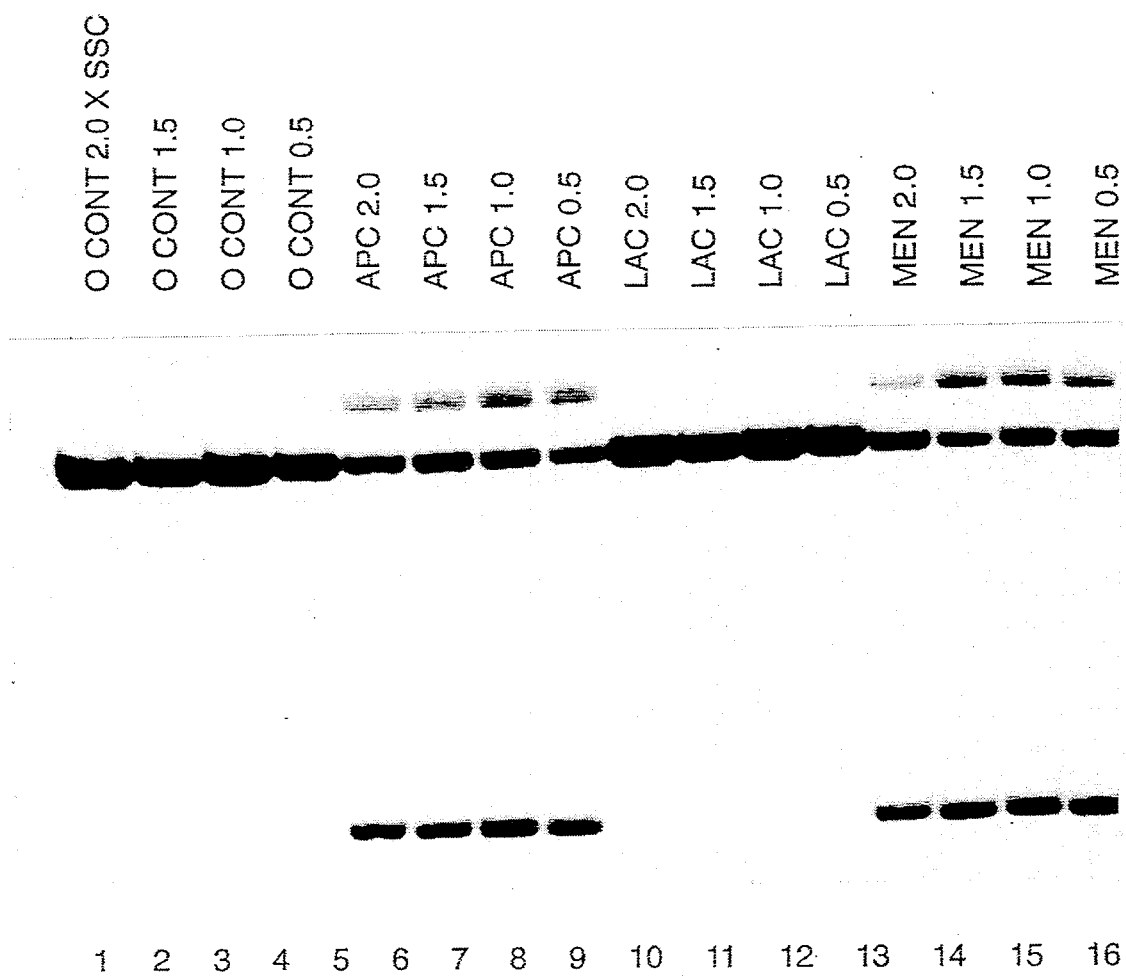
FIG. 1 presents initial binding studies using *N. gonorrhoeae* specific hybrid complexes.

Studies were undertaken to prepare appropriate materials for identification of *Neisseria gonorrhoeae*. The 16S rRNA gene for a specific strain of *N. gonorrhoeae* is known (Rossau et al., Nucl. Acids Res. 16:6227 (1988)). In experiments not described herein, the comparable DNA for 16S rRNA of specific strains of *N. meningitidis* and *N. lactamica* was sequenced. Comparison showed that nucleic acids 1262-1281 was non-homologous:

| | |
|---|---|
| AGCCGCGAGGCGGAGCCA | 1 (SEQ ID NO: 1) |
| AGCCGCG G CGGAGCCA | 2 (SEQ ID NO: 2) |
| AGCCGCGA CGATGCAT | 3 (SEQ ID NO: 3) |

Further experiments identified three other regions with a single base pair difference:

| | |
|---|---|
| ACACGTGGAATTCCACCTCCCTCTGAC | (SEQ ID NO: 4) |
| CCCACGCTTTCGGACATGAACGTCAGT | (SEQ ID NO: 5) |
| AGAGTGCCCAAACCGAATGATGGCAAC | (SEQ ID NO: 6) |

These sequences correspond to bases 661-687, 750-776, and 1125-1151, respectively, of the *N. gonorrhoeae* 16S rRNA gene minus strand In SEQ ID NO: 4, base 674 is "C", as compared to "T" in the two other Neisseria species. In SEQ ID NO: 5, base 763 is "A" as compared to the other two, and in SEQ ID NO: 6, base 1138 is "C" as compared to "T" for the other two strains. Sequences complementary to these are also useful.

Example 2

For the chosen sequence to be useful, they must identify *N. gonorrhoeae* as generally as possible, while not hybridizing to non-*N. gonorrhoeae* material. To test this with the sequences, probes were prepared therefrom via 5'-end labelling. Oligonucleotides corresponding to SEQ ID NOS: 4, 5 and 6 (1.0 ul, approx. 2.46 pmol) were mixed with 13.09 ul distilled $H_2O$, 2.0 ul of buffer, 3.66 ul of $\gamma$-$^{32}$P-ATP, and 0.25 ul $T_4$ polynucleotide kinase. The mixture was incubated at 37° C. for 30 minutes, after which 2.5 ul of 0.1M EDTA, at pH 8.0 was added. The mixture was kept on ice, at 4° C., until needed.

A panel of 39 strains of Neisseria were collected, and used with three controls. Chromosomal DNA was extracted from each strain following standard techniques. The DNA was then fixed to a nylon membrane, and used as target for the nucleotide sequences labelled supra. Hybridization was carried out at 65° C. overnight, after which dot blots were washed, dried, and subjected to standard autoradiography. Results are shown in Table 1, which follows:

TABLE I

| | Probes | | |
|---|---|---|---|
| Strain | 1 | 2 | 3 |
| 1. IUMC N.g. 1131 | − | − | − |
| 2. IUMC N.g. 1121 | + | + | + |
| 3. NRL N.g. JSK40 | + | + | + |
| 4. NRL N.g. 5767 | + | + | + |
| 5. NRL N.g. JSK127 | + | + | + |
| 6. NRL N.g. JSK237 | + | + | + |
| 7. NRL N.g. 5029 | + | + | + |
| 8. NRL N.g. 5001 | + | + | + |
| 9. NRL N.g. 8660 | + | + | + |
| 10. NRL N.g. 5766 | + | + | + |
| 11. NRL N.g. 85 | + | + | + |
| 12. IUMC N.g. 1124 | − | − | − |
| 13. IUMC N.g. 2686 | + | + | + |
| 14. IUMC N.g. 8035 | + | + | + |
| 15. IUMC N.g. DIS246 | + | + | + |
| 16. NRL N.g. DIS487 | + | + | + |
| 17. NRL N.g. RR21 | + | + | + |
| 18. NRL N.m. Z | − | − | − |
| 19. IUMC N.m. 515B | − | − | − |
| 20. IUMC N.m. 532 | − | − | − |
| 21. IUMC N.m. 512 | − | − | − |
| 22. NRL N.m. D | − | − | − |
| 23. IUMC N.m. UH | − | − | − |
| 24. NRL N.m. A | − | − | − |
| 25. IUMC N.m. 504B | − | − | − |
| 26. IUMC N.m. 517B | − | − | − |
| 27. IUMC N.m. 514C | − | − | − |
| 28. NRL N.lac. 30011 | − | − | − |
| 29. ATCC N.lac. 23970 | − | − | − |
| 30. IUMC N.perflava UH | − | − | − |
| 31. NRL N.flava 30008 | − | − | − |
| 32. NRL N.subflava 30017 | − | − | − |
| 33. IUMC N.pharn. 30661 | − | − | − |
| 34. NRL N.polys. 36088 | − | − | − |
| 35. NRL N.mucosa 36048 | − | − | − |
| 36. IUMC N.sicca 9913 | − | − | − |
| 37. IUMC N.catarr. 3443 | − | − | − |
| 38. IUMC N.catarr. 5903 | − | − | − |
| 39. NRL N.cinera 30003 | − | − | − |
| 40. E. coli MV1184 | − | − | − |
| 41. pUC 119 | − | − | − |
| 42. pUC 120 | − | − | − |

The results showed that all three sequences were specific for *N. gonorrhoeae*, and therefore presented a basis for further work.

Example 3

Initial experiments were carried out based upon the non-homologous sequence described by SEQ ID NO: 1. To perform these, a hybrid complex was prepared which contained, as the long binding probe an 80 nucleotide sequence. This long sequence was complementary to SEQ ID NO: 1, and began 49 bases from the 5' end of SEQ ID NO: 1. A signal probe was hybridized over the last 25 bases of the 3' end:

GAGGCGGAGCCAATCTCACAAAACC (SEQ ID NO: 7).

The 25 nucleotide probe was labelled in the manner described supra.

Displacement assays were carried out in the manner described by Diamond et al., U.S. Pat. No. 4,766,022 and Collins et al., EPA 167238. For completeness, however, the protocols are set forth. First, to hybridize the two components described supra, the following components were combined, in a 1.5 ml microfuge tube:

2×SSC (15.5 ul)
50% PEG (5.0 ul)
Binding probe (110 fm/ul) (2.5 ul)
Labelled signal (110 fm/ul) (2.0 ul).

Final volume was 25 ul, with a final salt concentration of 1.24×SSC and 10% PEG. The mixture was incubated at 37° C. for 60 minutes, and then kept on ice or at 4° C. until needed.

To assay for the analyte, 1.0 ul of hybrid complex was combined with 3 ul of distilled water, 4.0 ul of 25% PEG, 1.0 ul 20×SSC, and 10 ul of sample. The mixture was incubated at 50° C., for anywhere from 1–4 hours. Displacement of signal probe was determined via electrophoresis. The mixture was run through a 20% non-denaturing polyacrylamide gel (30% acrylamide solution: 66.6 ml; water: 21.3 ml; 3% ammonium persulfate: 2.1 ml; 10×TBE: 10.0 ml), filtered through a 0.45 um sterile filter unit. A total of 44 ul of TEMED was added, and the mixture was allowed to set. Sample was added (1500 volts, 2 hours, buffer 1×TBE; loading buffer: 30% glycerol plus dyes bromophenol blue and xylene cyanol).

The results, presented in FIG. 1, show that N. gonorrhoeae (lanes 5–8) gave a positive signal, whereas N. lactamica (lanes 9–12) did not. N. meningitidis (lanes 13–16), however, also gave positive results. This was attributable to the great degree of homology between N. gonorrhoeae and N. meningitidis, which has been reported to be as high as 98.5% for rRNA sequences.

Example 4

In view of the binding to N. meningitidis, alternate strategies were tested. These involved variations in the binding probe and the signal probe, with respect to size, and point of origin. The variations are presented infra, with "SDBP" referring to the binding probe, and "SDSP" to the signal probe. The first number refers to the length of the sequence, and the second number, its start relative to the 5' end of N. gonorrhoeae 16S rRNA gene.

In reviewing these data, it should be pointed out that "1262", which is the base of N. gonorrhoeae at which the non-homologous sequence begins, is referred to hereafter as "1213", in order for alignment with the E. coli 16S rRNA gene, as is standard in the art.

TABLE 2

| COMPLEXES TESTED | |
|---|---|
| I | SDBP-53-1243/SDSP-25-1268 |
| II | SDBP-43-1253/SDSP-25-1268 |
| III | SDBP-36-1261/SDSP-25-1268 |
| IV | SDBP-53-1243/SDSP-18-1271 |
| V | SDBP-43-1253/SDSP-18-1271 |
| VII | SDBP-36-1261/SDSP-18-1271 |
| VII | SDBP-53-1243/SDSP-18-1279 |
| VIII | SDBP-43-1253/SDSP-18-1279 |
| IX | SDBP-36-1261/SDSP-18-1279 |
| X | SDBP-32-1257/SDSP-25-1264 |
| XI | SDBP-36-1261/SDSP-25-1268 |
| XII | SDBP-32-1266/SDSP-25-1268 |
| XIII | SDBP-36-1261/SDSP-25-1271 |
| XIV | SDBP-32-1266/SDSP-25-1271 |
| XV | SDBP-32-1269/SDSP-25-1271 |
| XVI | SDBP-36-1261/SDSP-25-1273 |
| XVII | SDBP-32-1266/SDSP-25-1273 |
| XVIII | SDBP-32-1269/SDSP-25-1273 |
| XIX | SDBP-43-1260/SDSP-25-1276 |
| XX | SDBP-32-1266/SDSP-25-1276 |
| XXI | SDBP-32-1269/SDSP-25-1276 |

Of all hybrid complexes tested, only number 17, i.e., SDBP-32-1266/SDSP-25-1273 showed specificity. The initial binding region of this complex was 7 bases long, and had mismatches at positions 4 and 5 relative to non-gonorrhoeae Neisseria. The experiment indicated that the length of IBR is an important criterion in specificity.

Example 5

Figure 2:
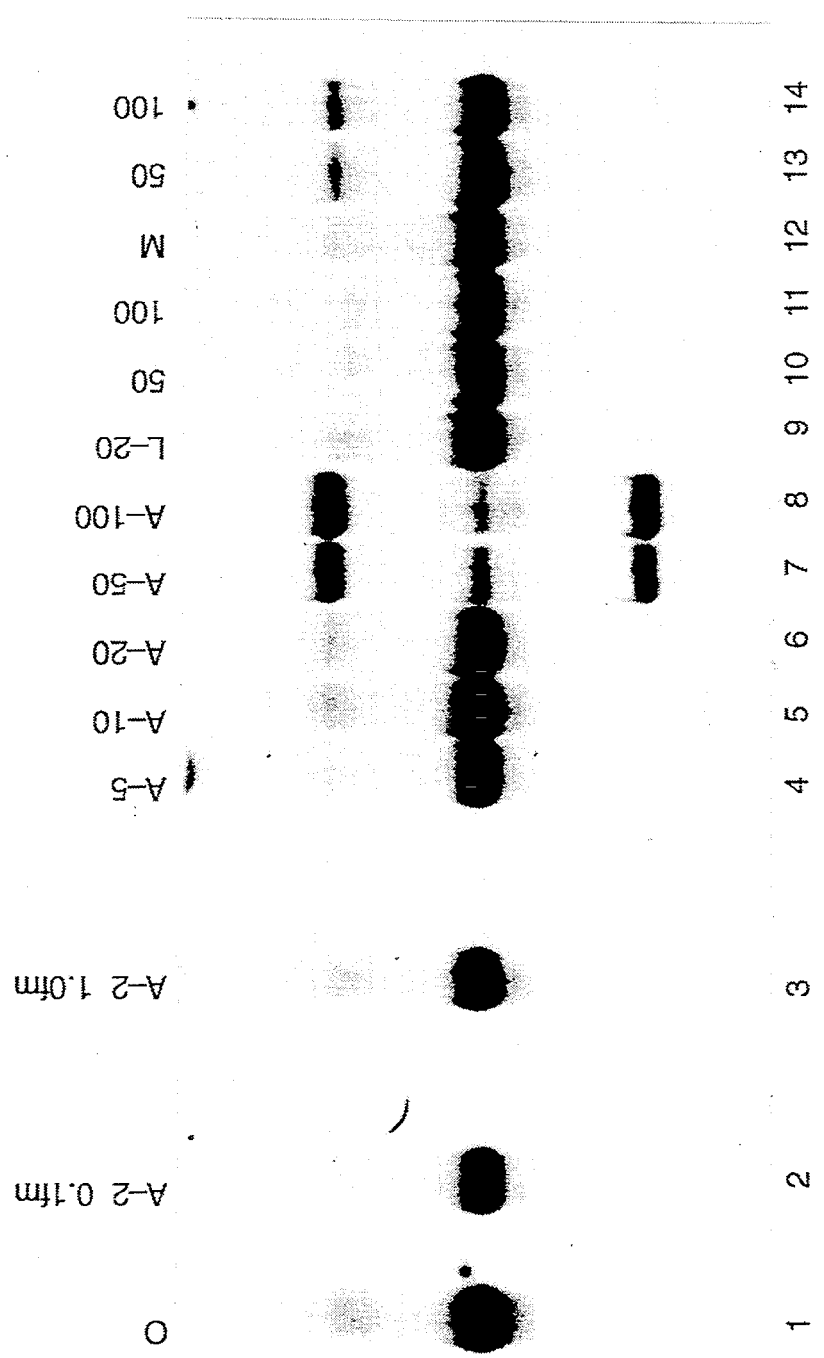
FIG. 2 shows results of studies identifying single base pair mismatching.

The observation described in Example 4, i.e., the importance of IBR length, was tested in subsequent experiments. In these, synthetic N. gonorrhoeae analytes were prepared, wherein single point mutations were incorporated. The SDBP-32-671/SDSP-25-678 complex was used, following the protocols given supra. FIG. 2 shows that resolution down to a single base pair mismatch was possible. This is an advance over the current level of resolution in the art, and provides an opportunity, for the diagnosis of diseases caused by point mutations (e.g., sickle cell anemia), as well as the differentiation of closely related organisms, including viruses.

Example 6

Figure 3:
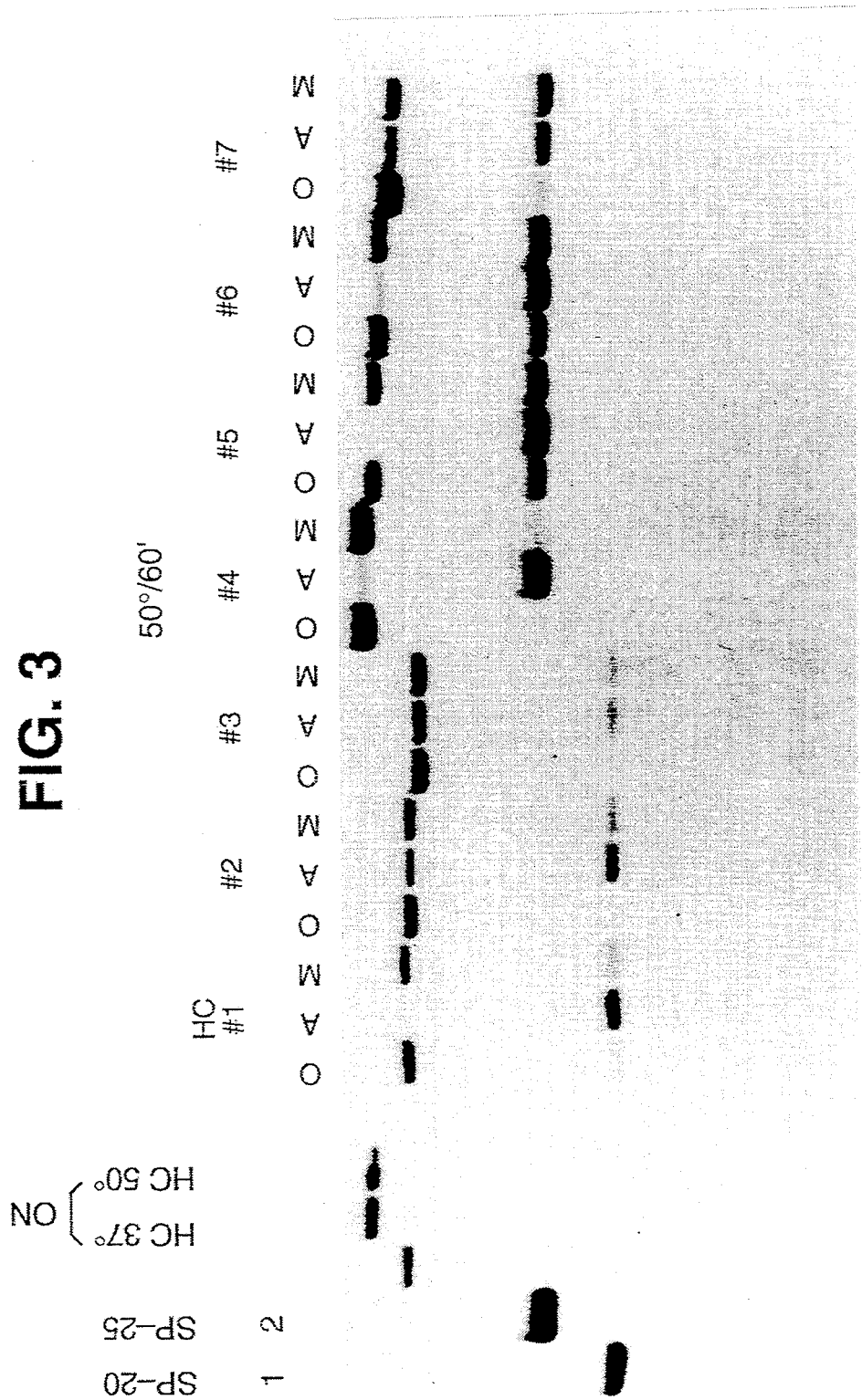
FIG. 3 presents additional displacement studies.
Figure 4:
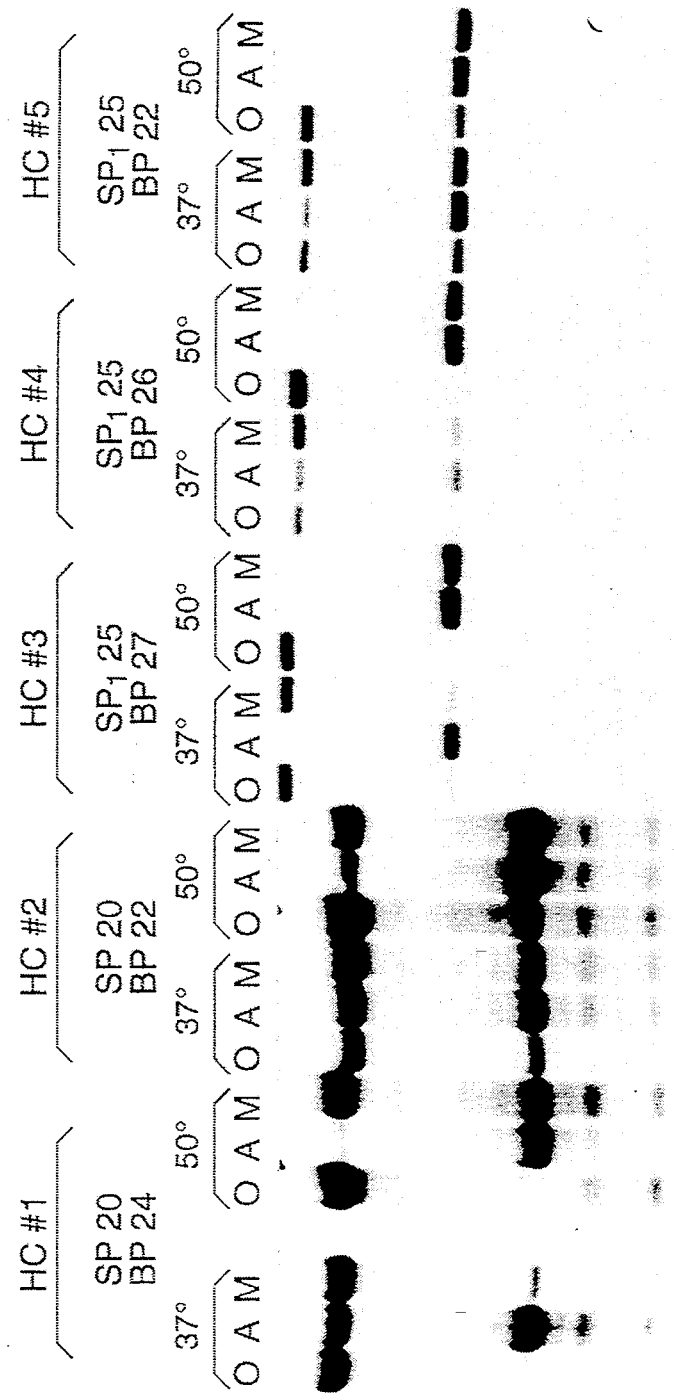
FIG. 4 shows further displacement studies.
Figure 5:
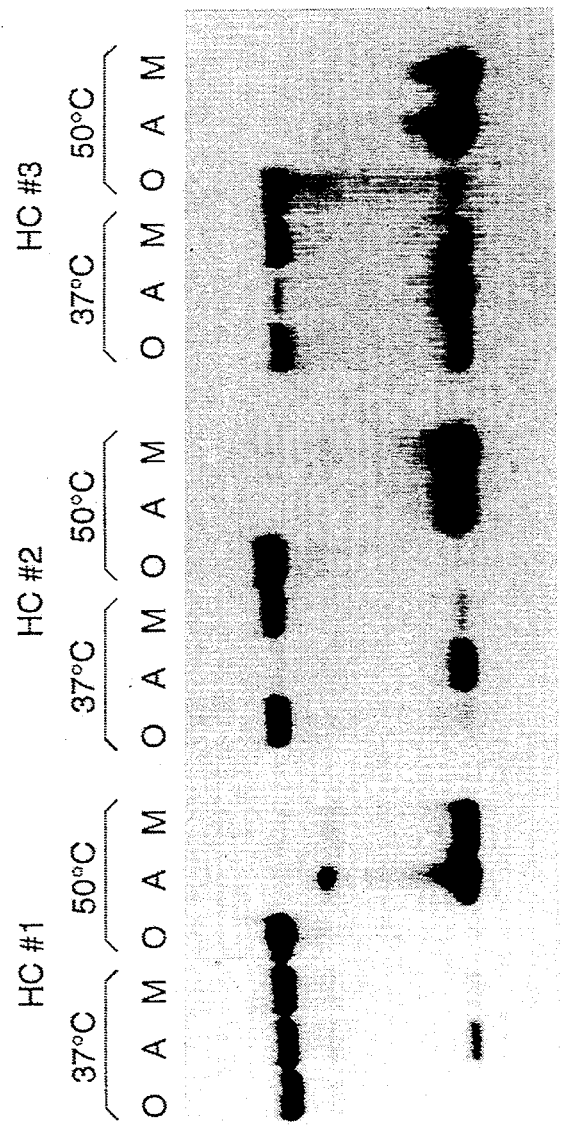
FIG. 5 presents additional displacement studies.

The examples described supra generally required about 10 minutes for completion. Attempts were made to improve the kinetics of the assay. To carry these out, compositions were prepared based upon the sequence corresponding to bases 661–687 of N. gonorrhoeae, which, as indicated supra, differs from other Neisseria organisms at base 674. A number of complexes were prepared and were tested with controls, synthetic N. gonorrhoeae reagent, and with synthetic N. meningitidis reagent. The displacement assay involved use of 50 fmol of sample, and 10 fmol of hybrid complex. The materials were incubated at either 37° C. or 50° C. for one hour. The results of the displacement are shown in FIGS. 3, 4, and 5. The results can be summarized, however, in the following Table 3:

| PERFORMANCE DATA - SELECTED ARCHITECTURES AT THE "674 SITE" | | | | | |
|---|---|---|---|---|---|
| Binding probe | Signal probe | IBR Length | Mismatch position[a] | Selectivity[b] | |
| | | | | 37° C. | 50° C. |
| 32-671 | 25-678 | 7 | 4 | ++++ | − |
| 32-671 | 20-677 | 6[c] | 4 | ++ | − |

-continued

PERFORMANCE DATA - SELECTED ARCHITECTURES AT THE "674 SITE"

| Binding probe | Signal probe | IBR Length | Mismatch position[a] | Selectivity[b] 37° C. | 50° C. |
|---|---|---|---|---|---|
| 32-671 | 27-678 | 7[d] | 4 | + | − |
| 27-671 | 25-677 | 7 | 4 | +++ | − |
| 27-671 | 20-677 | 6 | 4 | +++ | ++ |
| 26-672 | 25-678 | 6 | 3 | ++ | − |
| 26-672 | 20-677 | 5 | 3 | + | − |
| 25-673 | 25-678 | 5 | 2 | − | − |
| 25-673 | 20-677 | 4 | 2 | − | − |
| 25-672 | 25-678 | 6 | 3 | + | − |
| 25-672 | 20-677 | 5 | 3 | + | +++ |
| 24-671 | 25-678 | 7 | 4 | +++ | − |
| 24-671 | 20-677 | 6 | 3 | ++ | + |
| 24-671 | 17-678 | 7 | 4 | ++++ | ++ |
| 22-672 | 25-678 | 6 | 3 | +++ | − |
| 22-672 | 20-677 | 5 | 3 | − | + |

[a]From 3' end of binding probe.
[b]Selectivity scale: −, no selectivity; + to ++++, poor to good selectivity. Displacement reaction for 60 min at the indicated temperature.
[c]8-base overhang at the 5' and may decrease selectivity.
[d]7-base overhang at the 5' and may decrease selectivity.

The two complexes which gave the best results were SDBP-32-671/SDSP-25-678 and SDBP-24-671/SDBP-17-678, both of which had IBRs 7 bases in length. These complexes were then used in kinetic studies, and it was found that, when incubated at 45° C., using the conditions set forth in the prior examples, the displacement reaction was completed within five minutes.

Example 7

Studies were carried out to determine the sensitivity of the assay. In these experiments, 1 attamol ($1 \times 10^{-18}$ mol) of complex was combined with 5–10 fold excesses of analyte at low stringency conditions, sensitivities of about 1 attamol were observed.

Figure 6:
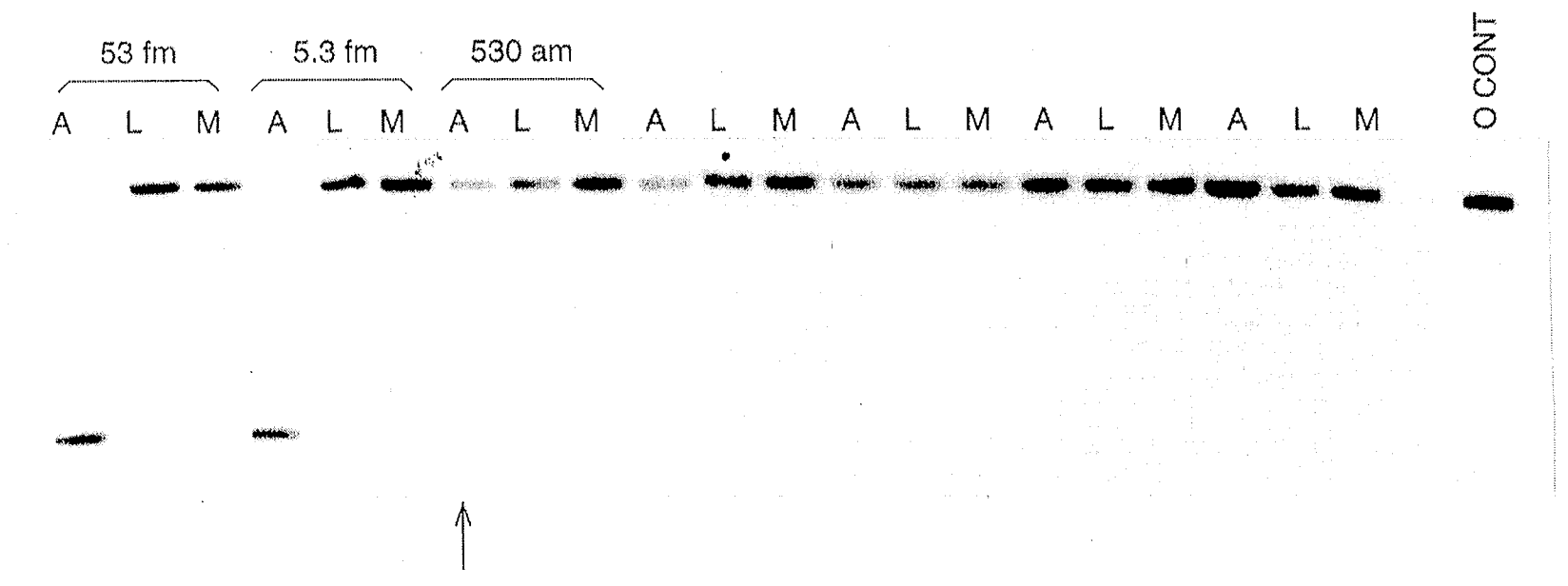

Stringent conditions were also tested (0.22×SSC, 10% PEG, 375 attamol hybrid, 0.005 attamol—53 fmol sample). Under these conditions, sensitivity to about 530 attamol was observed, as is seen from, e.g., FIG. 6. This figure shows results obtained with amounts that range from less than stochiometric up to 100 fold excesses.

Example 8

Stability of hybrids was studied in two different ways. The first approach used preformed hybrid complex made as described supra, which were stored at 4° C. Aliquots were then removed periodically, and assayed via gel electrophoresis. No dehybridization was found over a three week period. In a variation on this, the hybrid complexes were studied at 50° C., and less than 10% "dehybridization" was observed after 24 hours.

A second methodology for determining stability involved formation of the hybrids, evaporation to dryness, and storage at 4° C. Once a week, over a five week period, residues were redissolved in hybridization buffer, aliquots were removed, and gel electrophoresis was carried out. No dehybridization was observed even after five weeks.

Example 9

In these experiments rRNA from Neisseria was analyzed using hybrid complexes SDBP-32-671/SDSP-25-678 and SDBP-24-671/SDSP-17-678. Both probes were $^{32}$P labelled.

First of all, RNA was isolated from various Neisseria strains. To do this, 200 ml of each sample were grown to mid log phase. Then, 20 ml of "buffer A" (200 mM Tris, pH 8.0, 20 mM EDTA, 20 mM Na$_3$N, 20 mM aurintricarboxylic acid) was added to each culture. Cultures were pelleted, and pellets were resuspended in 2 ml of "STET" buffer (8% sucrose, 5% Triton X-100, 5 mM EDTA, 50 mM Tris, pH 7), with 10 mM vanadylribonucleoside complex (VRC). Suspensions were extracted with phenol chloroform (1:1). Phases were separated by centrifugation. The aqueous phase was removed and then precipitated with 0.1 volume of 3M sodium acetate and two volumes of ethanol.

Precipitates were concentrated by centrifugation at 10,000 RPM for 15 minutes. Pellets were then resuspended in 2 ml of DEPC-treated sterile water with 10 mM VRC. The mixture was extracted twice with phenol chloroform, and precipitated.

After centrifugation, resulting pellets were resuspended in 2 ml of DEPC-treated sterile water, and 1 g CsCl. Each mixture was then layered onto a 0.75 ml cushion of 5.7M CsCl/100 mM EDTA, pH 7, then layered with ~1 ml of glycerol. The rRNA was then pelleted overnight by centrifugation at 40,000 RPM. Glycerol and the CsCl cushion were removed, and the RNA pellets resuspended in 400 ul of DEPC treated sterile water. RNA was precipitated with sodium acetate and ethanol.

The precipitate was concentrated by centrifugation and resuspended in 300 ul of DEPC treated water. Optical densities were taken and the RNA was frozen in aliquots at −20° C. Homogeneity was checked by electrophoresing an 11.25 ul aliquot on 1% formaldehyde/agarose gel, followed by ethidium bromide visualization. E. coli rRNA was a control. Average yields were 2.9 mg for N. gonorrhoeae, 2.7 mg for N. meningitidis, and 3.1 mg for N. lactamica. These samples contained both 16S and 23S rRNA, with the ratio being about $\frac{1}{3}:\frac{2}{3}$.

Figure 7:
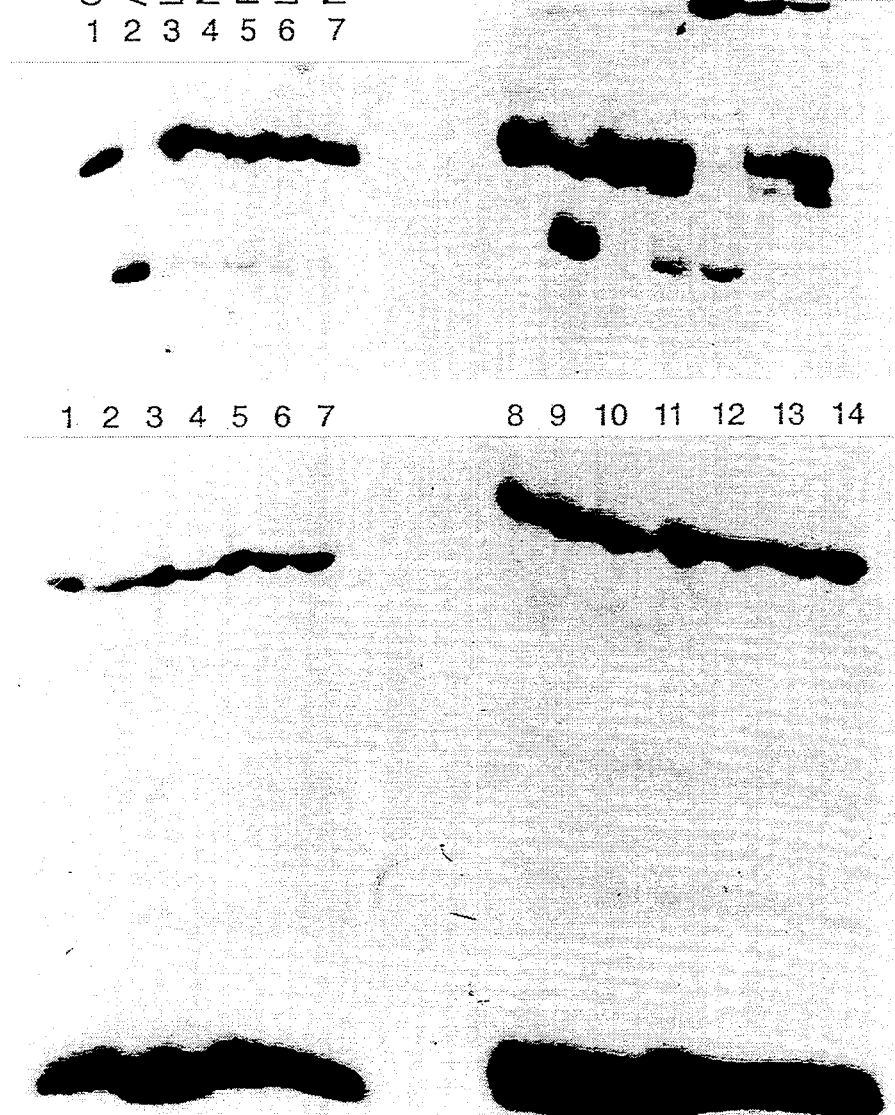
FIG. 7 shows specificity of the assay for extracted RNA.
Figure 8:
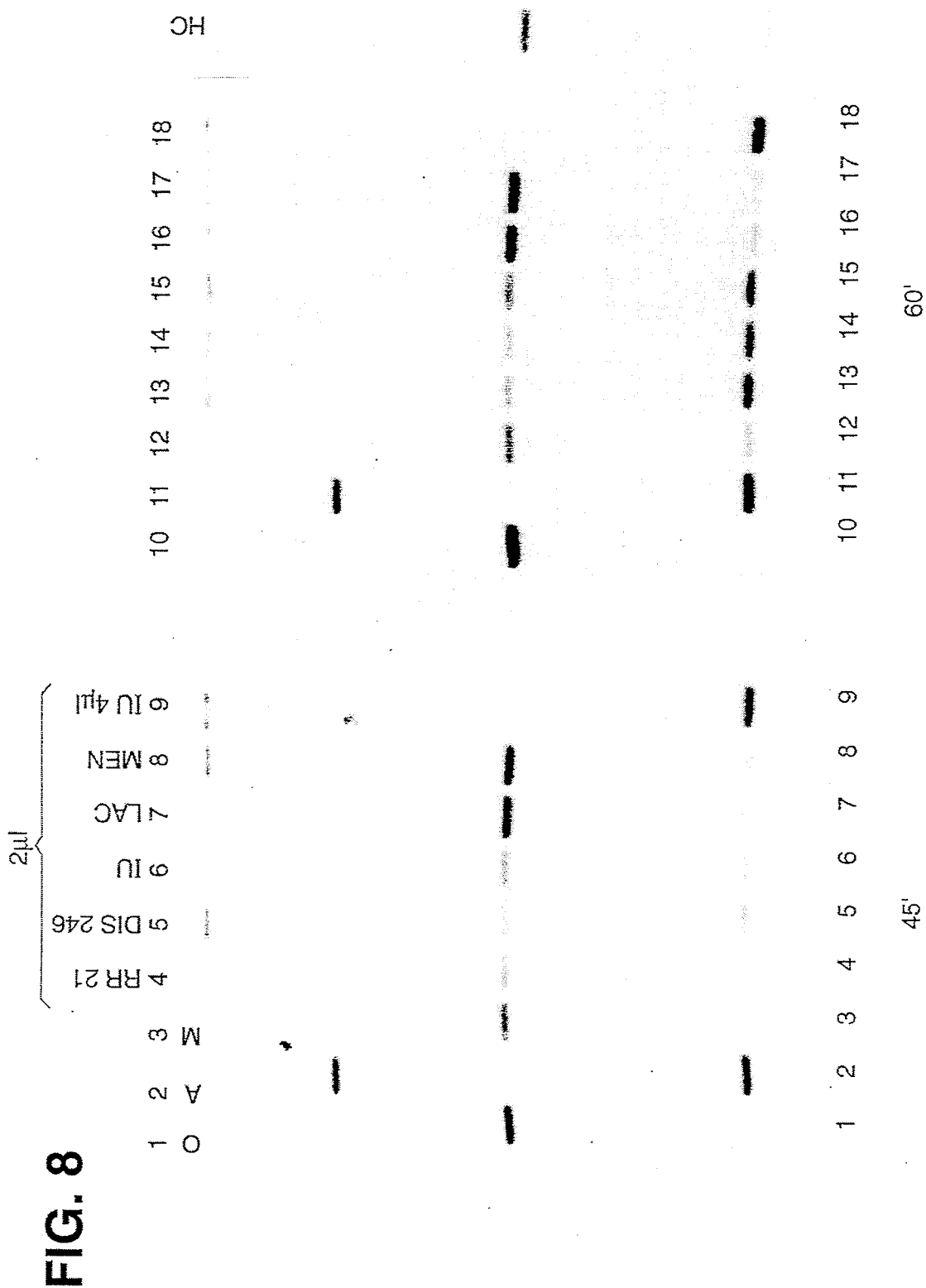
FIG. 8 also shows specificity for extracted RNA.

The protocols for hybridization as described supra were carried out. The hybrid complexes listed in this example were used. FIGS. 7 and 8 both show displacement for N. gonorrhoeae, but not N. meningitidis or N. lactamica.

To perform a strand displacement on a rapidly lysed sample of Neisseria in accordance with the invention, Neisseria stains were grown on chocolate agar plates, and individual colonies were transferred to sterile 1.5 ml microfuge tubes containing 50 ul GTE (glucose, Tris, EDTA/lysozyme solution). This mixture was vortexed vigorously, and incubated on ice for five minutes. A 50 ul aliquot of gram negative lysing solution (Collins, EPA 167238) was added, and the sample was vortexed for 15 seconds. The samples were then ready for strand displacement assays.

Figure 9:
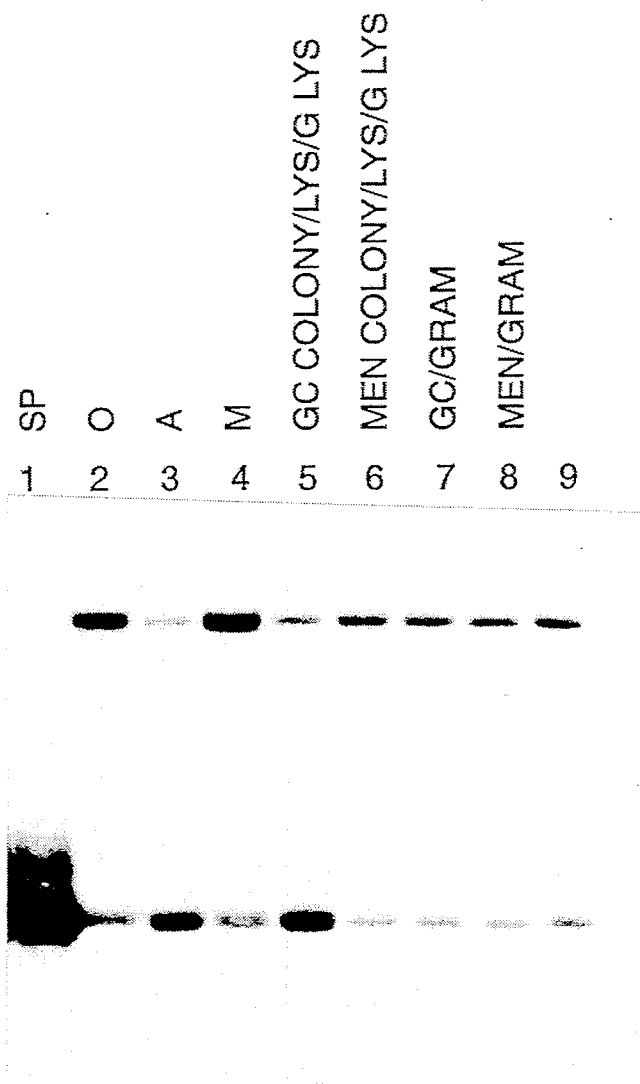
FIG. 9 depicts results secured with samples of lysed bacteria.

The results, shown in FIG. 9, demonstrate the efficacy of the strand displacement assay with the lysed sample.

Example 10

Examples 1–9 show the feasibility of using the strand displacement assay discussed herein for identifying N. gonorrhoeae. The assay was also tested for identifying sickle cell anemia linked sequences.

Oligonucleotides were prepared in accordance with Bakloriti et al., Blood 74:1817–1822 (1989) i.e.:

| | | |
|---|---|---|
| SCASP-1: | 5'-GAAGTCTGCCGTTACTG-3'<br>Signal Probe | (SEQ ID NO: 8) |
| SCABP-1: | 5'-CAGTAACGGCAGACTTCTCCTCAG-3'<br>(binding probe, normal) | (SEQ ID NO: 9) |
| SCABP-2: | 5'-CAGTAACGGCAGACTTCTCCACAG-3'<br>(binding probe, disease) | (SEQ ID NO: 10) |
| SCAAN-1 | 5'-CTGACACAACTGTGTTCACTAGCAACTTCAAACAGACACCAT<br>GGTGCACCTGACTCCTGAGGAGAAGTCTGCCGTTACTG-3'<br>(analyte, normal) | (SEQ ID NO: 11) |
| SCAAN-2 | 5'-CTGACACAACTGTGTTCACTAGCAACTTCAAACAGACACCAT<br>GGTGCACCTGACTCCTGTGGAGAAGTCTGCCGTTACTG-3'<br>(analyte, disease) | (SEQ ID NO: 12) |

Figure 10:
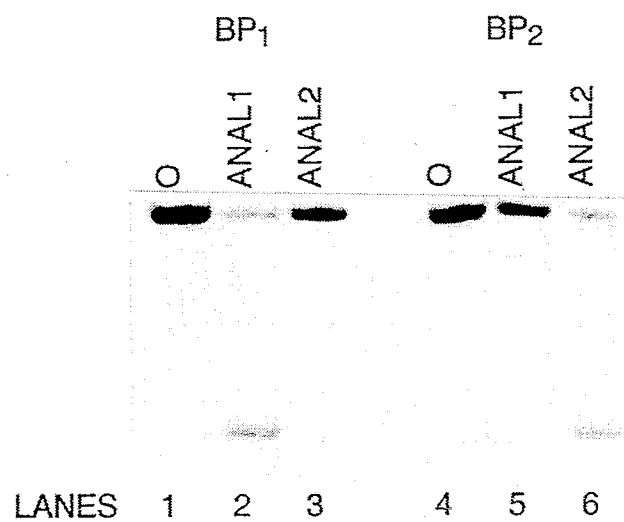
FIG. 10 shows results of studies on sickle cell anemia DNA.

The difference between normal and disease analytes is found at base 60 (A for normal; T for disease), and the difference in binding probe 4 bases from the 3' end (T for normal; A for disease). Reactions were carried out, using the conditions as set forth in the Neisseria assays, at 37° C. Lanes 1–3 of FIG. 10 show the use of normal binding probe with diseased analyte, whereas lanes 4–6 show the use of the disease probe, also with normal and disease analyte. Definitive identification of the point mutation was observed. Further, no cross reactivity was observed when the two analytes were compared. Normal hemoglobin model sequence showed no displacement with sickle cell hemoglobin model analyte, and vice versa.

Example 11

Examples 1–10 detail strand displacement assays which take place in solution. In practice, a solid phase based assay system is most desirable, as the medical office and small laboratory, e.g., would find such systems quite desirable.

Latex beads with streptavidin coatings were used as the solid phase, it being noted that many methodologies for the attachment of this binder and the related molecule avidin are well known. These were used in connection with biotin labelled hybrid complexes. These complexes were the SDBP-32-671/$^{32}$P-SDSP-25-678 and the SDBP-32-1266/$^{32}$P-SDSP-25-1273 materials described supra. An amino linkage was attached to the SDBP, following manufacturer's instructions (see "Applied Biosystems User Bulletin 49"), and the resulting material was biotinylated. To do this, the amino-linked oligonucleotide was dried, and reconstituted in 75 ul of 0.25M Tris-HCl, at pH 7.6. A 1.0 mg sample of biotin-NHS ester was then dissolved in 75 ul of DMF, and the two materials were mixed and vortexed overnight at room temperature. The DMF was removed by dialysis, and the resulting material concentrated by rotary evaporation. The concentrate was dissolved in distilled water. HPLC analysis showed that the biotin linkage had taken place.

Once the biotinylated probes and streptavidin beads were available, two different methodologies could be followed to carry out a strand displacement assay. One format calls for carrying out the reaction between target analyte and hybrid complex, after which streptavidin labelled beads were added to collect any unreacted complex. Similarly, the complexes were preincubated with the beads, and strand displacement studied by adding the solid phase bound complex to the sample, and allowing strand displacement to proceed thereafter.

Using the first option, solution phase reactions as described supra were allowed to take place after which the streptavidin labelled beads were added, and incubated for two minutes. An aliquot of material was then added to a gel for examination.

Figure 11:
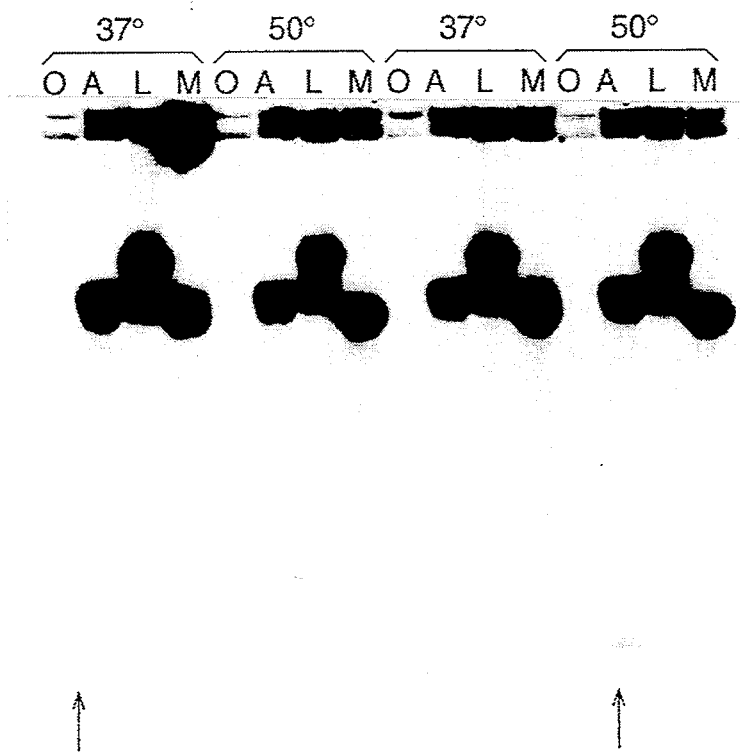
FIG. 11 presents data using a solid phase based assay.

Following the second alternative, beads were mixed with the biotinylated hybrid complex (SDBP-32-1266/$^{32}$P-SDSP-25-1273) and incubated for two minutes after which these were added to sample. Again, an aliquot of sample was added to the gel after reaction. In both formats, tests were carried out using two sets of parameters (37° C. 90 minutes incubation, or 50° C., 20 minutes incubation). In FIG. 11, lanes 1–8 show results where the assay was carried out in the presence of the beads, while lanes 9–16 are the results obtained when beads were added after reaction. In all cases, 9 fmol of complex and 50 fmol of analyte were used. Only *N. gonorrhoeae* model analyte produced displacement, both *meningitidis* and *lactamica* models showing none.

Figure 12:
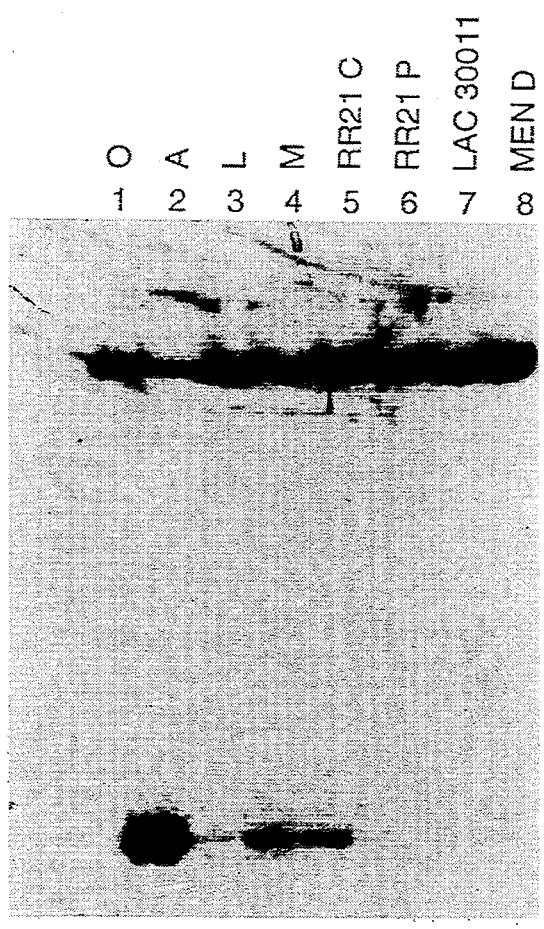
FIG. 12 also shows displacement assays using beads.

In another set of experiments, the displacement reaction was carried out using 10 fmol of biotin labeled SDBP-32-671/$^{32}$P-SDSP-25-678, incubated at 50° C. for 30 minutes, followed by chilling on ice before the coated beads were added. Synthetic analytes were tested, as were crude RNA extracts. FIG. 12 shows these results. Complete reactions took place for the synthetic *N. gonorrhoeae*, and a partial reaction for *N. meningitidis* (lanes 2 and 4, respectively). Only crude *N. gonorrhoeae* extract showed reaction (lane 5), the other crude extracts (lanes 6–8) showing no reaction.

Example 12

Experiments were also carried out to test the displacement assay when used in connection with a nitrocellulose membrane. In these experiments, a nitrocellulose membrane (5 um, MSI) had reaction mixture applied about 0.5 cm from the bottom. Hybridization buffer was then added until the solvent front had migrated about 2.5 cm. Strips were covered, and autoradiography was carried out.

Figure 13:
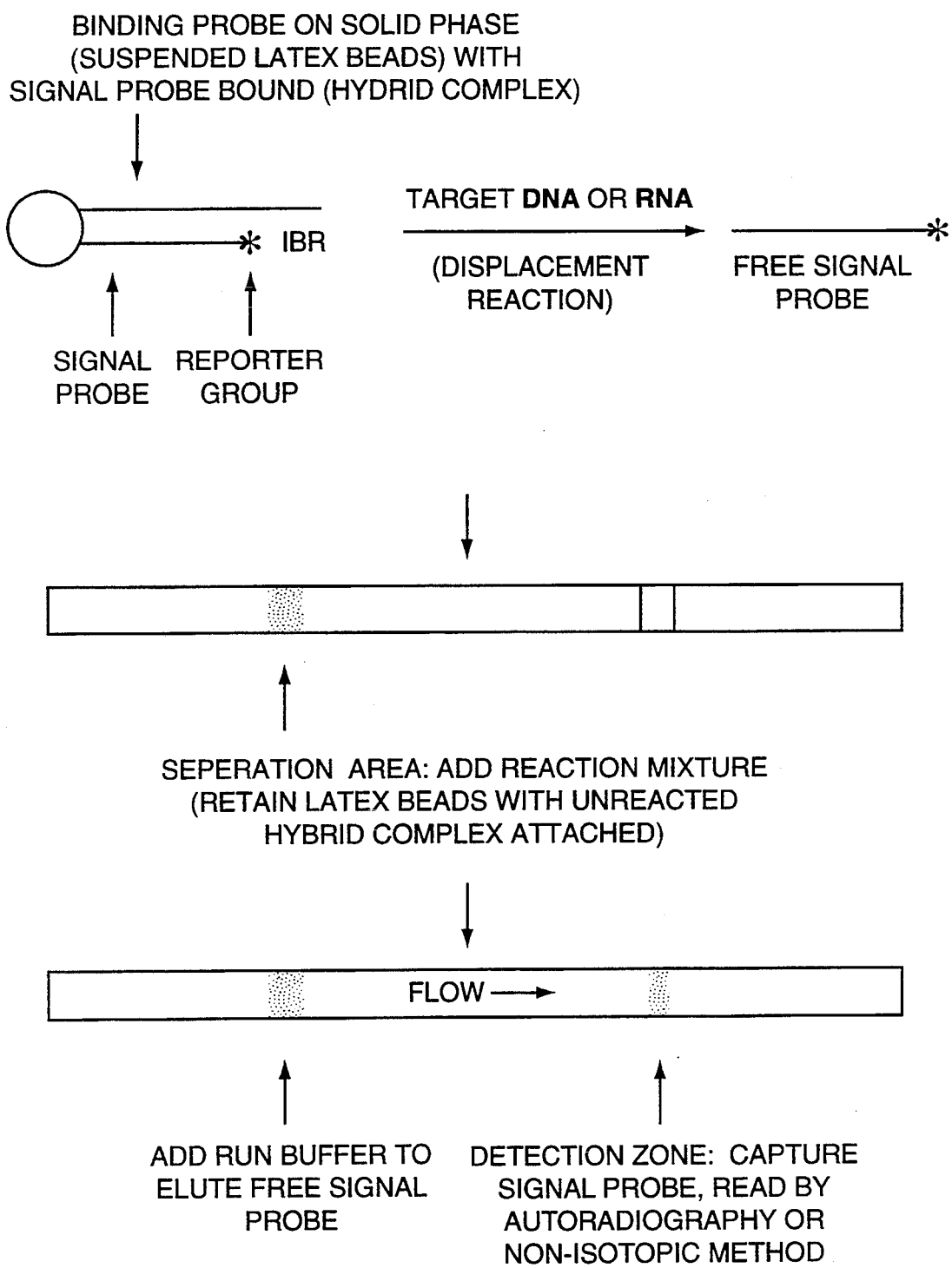
FIG. 13 is a diagram of a typical strip format assay.
Figure 14A:
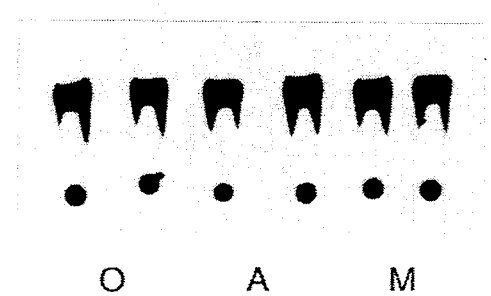
FIG. 14 shows results obtained using the strip format.
Figure 14B:
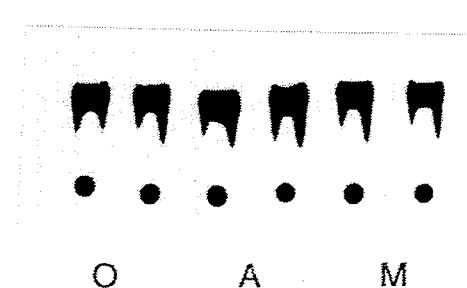
Figure 14C:
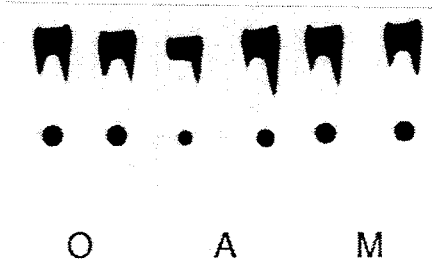
Figure 14D:
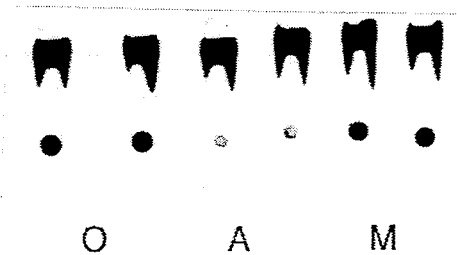

FIG. 13 shows a typical system for a strip format assay. In the experiments discussed herein, the biotin labeled hybrid complex SDBP-32-671/$^{32}$P-SDSP-25-678 (10 fmol), was combined with various Neisseria analytes. Reaction temperature was 50° C. Aliquots were removed at 2, 5, and 10 minutes interval, and added to streptavidin coated beads, and stored on ice. The mixtures were applied in duplicate to the strips described supra, and subjected to autoradiography.

FIG. 14 shows the results. In the control reaction, there was no analyte, and hybrid complex remains at the point of application. When correct analyte ("A" in the figure) is added, there is displacement, as is indicated by the gradual disappearance of radioactivity. This does not occur with *N. meningitidis* ("M" in the figure).

Example 13

Figure 15:
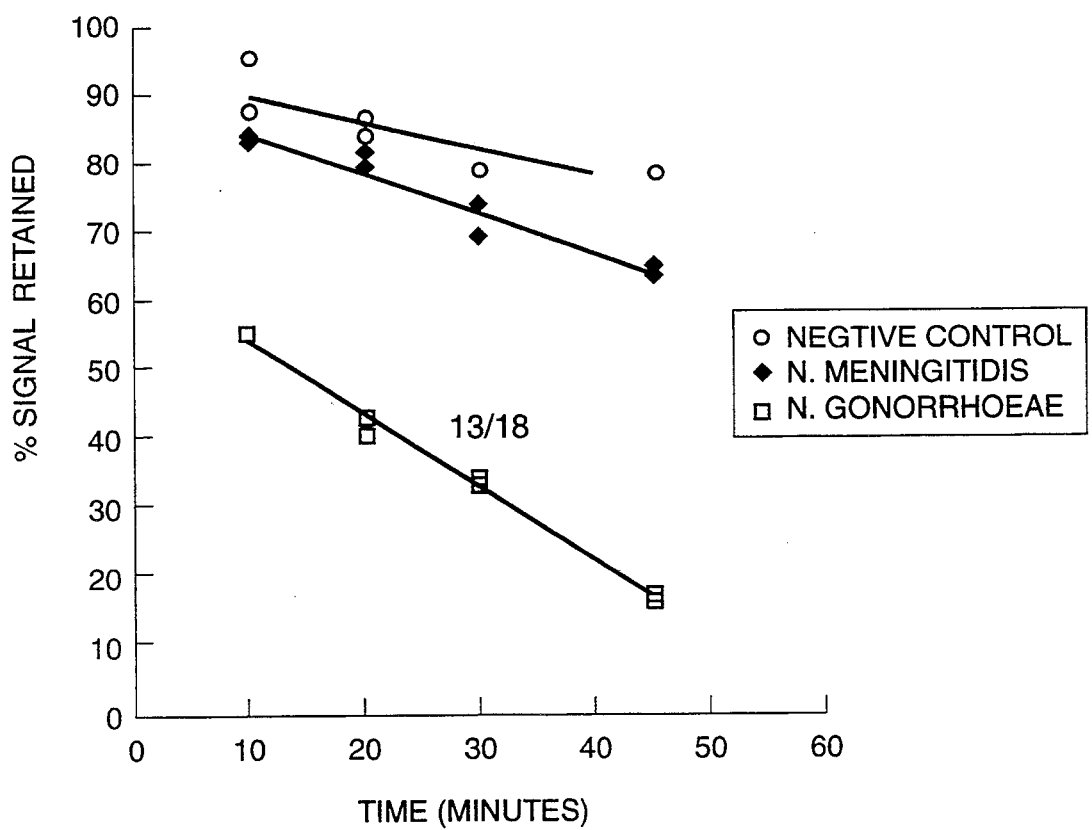
FIG. 15 shows results obtained in a solid phase kinetics assay.
Figure 16:
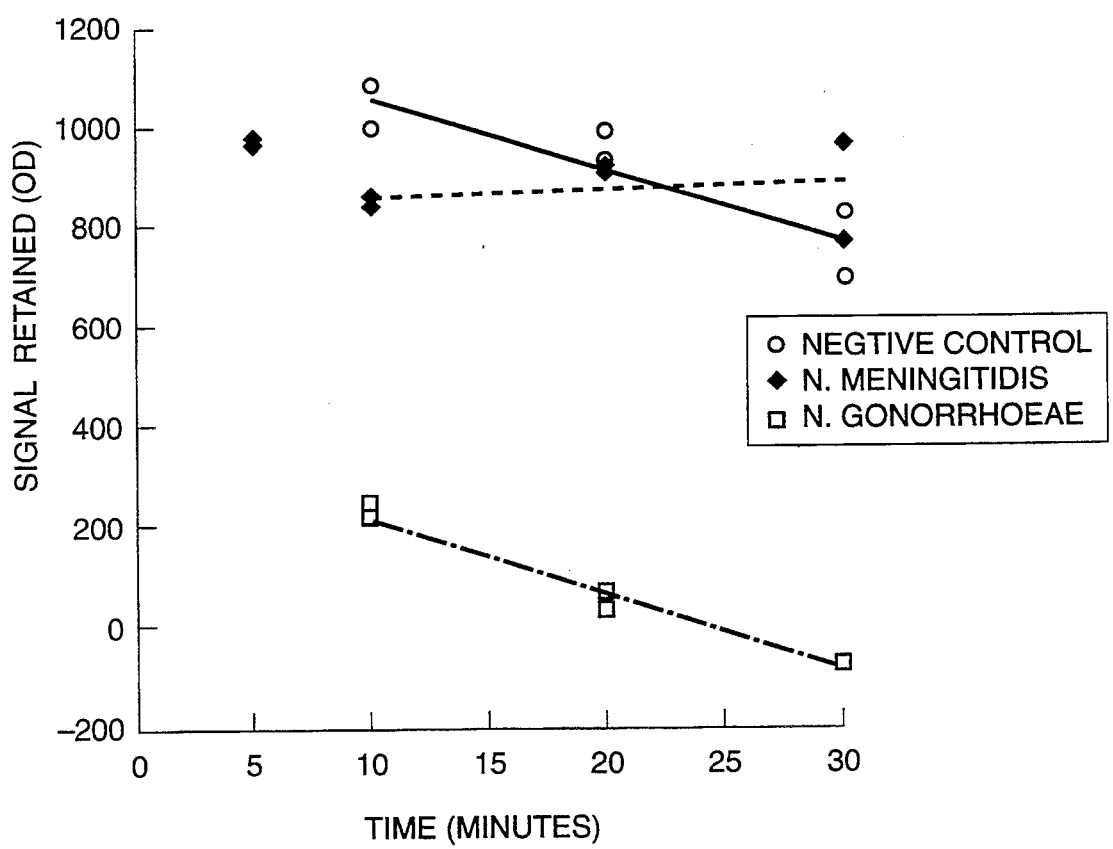
FIG. 16 also shows results from a solid phase kinetics assay.

Reaction kinetics were compared for systems where beads were added after displacement with the complex. All parameters were as in example 12. The results, presented in FIGS. 15 and 16, show that when the beads were added with the complexes, 80% displacement occurred after 40 minutes. On the other hand, when beads were added later, 80% displacement occurred after only 10 minutes. In view of the marked difference in kinetics, subsequent experiments employ the faster reaction system.

Example 14

Figure 17:
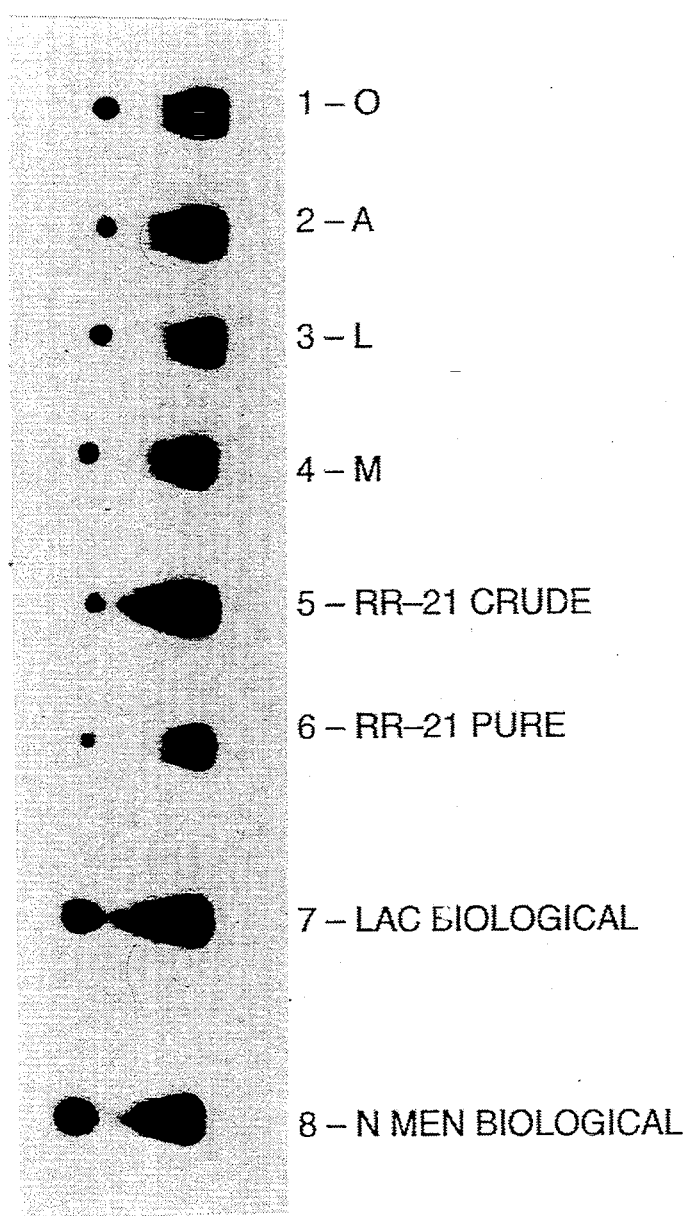
FIG. 17 shows results of a solid phase assay using crude rRNA extracts.

The strip based assays described supra used synthetic analyte. Feasibility of the assay using rRNA was tested. The probe complex used was that of examples 11-13, and the analyte was either RNA extracted in the manner described supra, or synthetic analytes. The protocols of the assay were those of examples 12 and 13. The results, as will be seen from FIG. 17, show that crude nucleic acid mixture (*N. gonorrhoeae* RR21) and pure RNA show displacement, whereas pure *N. lactamica* RNA and pure *N. meningitidis* RNA did not.

Example 15

Figure 18:
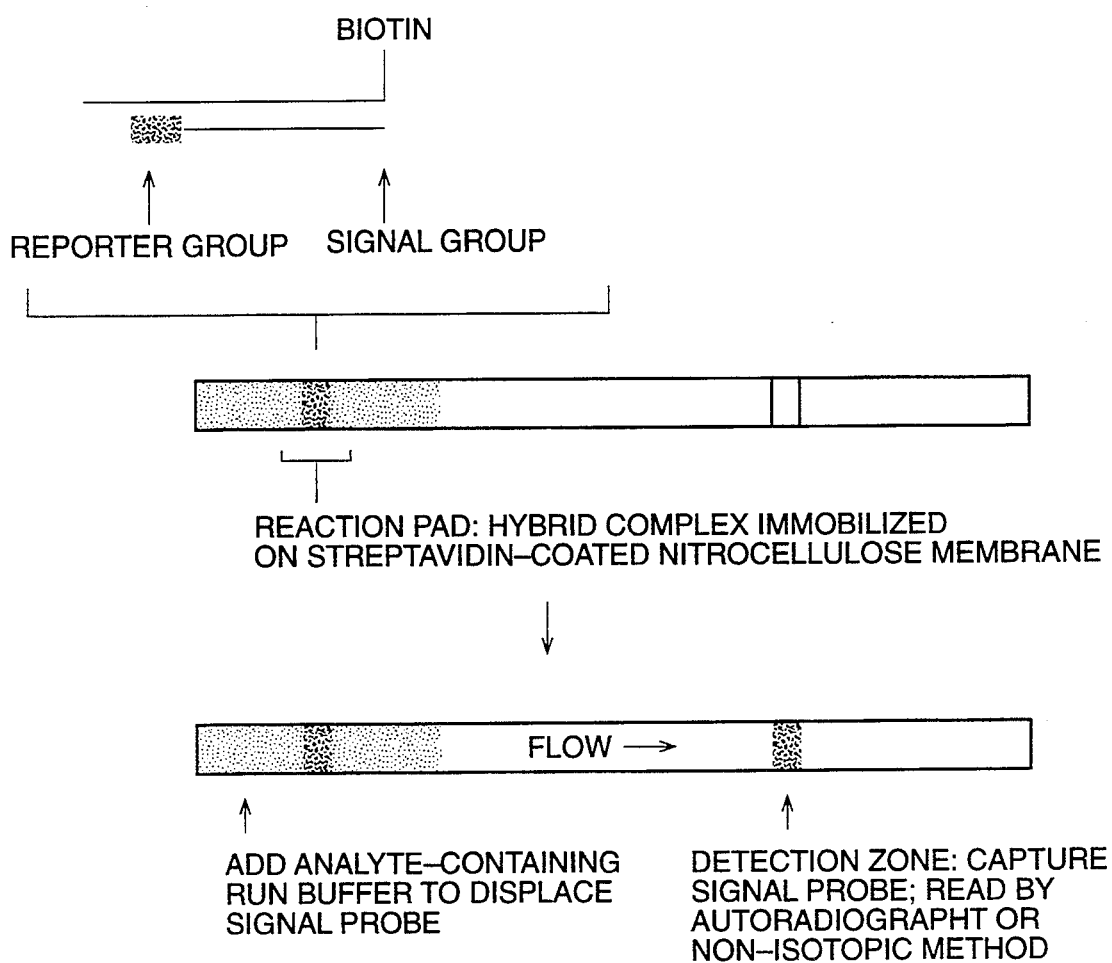
FIG. 18 presents a model for an on strip capture assay.
Figure 19:
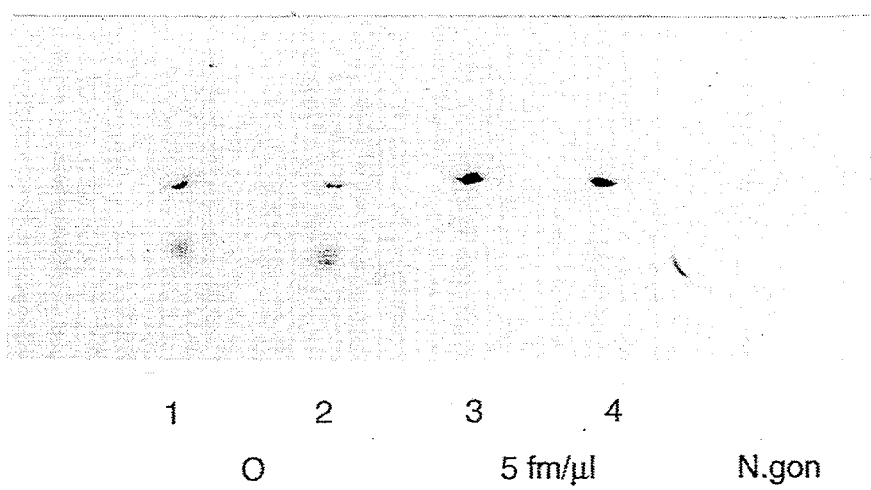
FIG. 19 shows results secured using an on strip capture assay.

A modification of the strip methodology discussed supra was developed, in order to simplify the reaction steps. This modification will be referred to as the direct, on-strip capture methodology as shown in FIG. 18. Essentially, portions of nitrocellulose strips were coated with thermal-BSA streptavidin, using standard techniques. Standard solution phase displacement reactions were carried out, using the biotinylated hybrid complexes of examples 11-14. After displacement, reaction aliquots were spotted on the precoated strip (2 fmol probe, and 0.1, 0.3, 1.0, 3, 10.0 and 30.0 fmol analyte). Incubation was for one hour at 50° C. Each analyte was run in duplicate, and controls in triplicate. Strips were chromatographed after five minutes, and autoradiographed, as shown in FIG. 19. At all concentrations, there was displacement, although the control also showed some displacement.

Example 16

The probes represented by SEQ ID NOS: 4, 5 and 6, and their complements are useful in assays other than strand displacement assays. They were tested extensively, using over 200 clinical isolates of *Neisseria gonorrhoeae*, selected from around the world.

To carry out the probe studies, 25 ul cultures of Neisseria strains were grown, and genomic DNA was extracted using standard methodologies. The DNA was purified, and checked on agarose for purity and integrity. Once this was done, 10 ug samples were applied to nylon membranes, again using standard technique. Probe samples were then added (approximately 3×10$^5$ counts of $^{32}$P labelled probe), followed by overnight hybridization at 65° C. The membranes were washed and exposed to film.

Results are presented in accompanying Table 4. The notations in the Table correspond to SEQ IDs as follows:

| Probe | SEQ ID NO: |
|---|---|
| 1A | complement to 4 |
| 2A | 4 |
| 3 | complement to 6 |
| 4 | 6 |
| 5 | complement to 5 |
| 6 | 5 |
| R102 | control sequence (see, e.g., European Patent Application 272,009) |

TABLE 4

DNA DOT BLOT SUMMARY

| STRAIN | r102 | 1A | 2A | 3 | 4 | 5 | 6 |
|---|---|---|---|---|---|---|---|
| 1 | + | + | + | + | + | + | + |
| 2 | + | + | + | + | + | + | + |
| 3 | + | + | + | + | + | + | + |
| 4 | + | + | + | + | + | + | + |
| 5 | + | + | + | + | + | + | + |
| 6 | + | + | + | + | + | + | + |
| 7 | + | + | + | + | + | + | + |
| 8 | + | + | + | + | + | + | + |
| 9 | + | + | + | + | + | + | + |
| 10 | + | + | + | + | + | + | + |
| 11 | + | + | + | + | + | + | + |
| 12 | + | + | + | + | + | + | + |
| 13 | + | + | + | + | + | + | + |
| 14 | + | + | + | + | + | + | + |
| 15 | + | + | + | + | + | + | + |
| 16 | + | + | + | + | + | + | + |
| 17 | + | + | + | + | + | + | + |
| 18 | did not grow | | | | | | |
| 19 | + | + | + | + | + | + | + |
| 20 | + | + | + | + | + | + | + |
| 21 | + | + | + | + | + | + | + |
| 22 | + | + | + | + | + | + | + |
| 23 | + | + | + | + | + | + | + |
| 24 | + | + | + | + | + | + | + |
| 25 | + | + | + | + | + | + | + |
| 26 | + | + | + | + | + | + | + |
| 27 | + | + | + | + | + | + | + |
| 28 | + | + | + | + | + | + | + |
| 29 | + | + | + | + | + | + | + |
| 30 | + | + | + | + | + | + | + |
| 31 | did not grow | | | | | | |
| 32 | + | + | + | + | + | + | + |
| 33 | + | + | + | + | + | + | + |
| 34 | contaminated | | | | | | |
| 35 | + | + | + | + | + | + | + |
| 36 | + | + | + | + | + | + | + |
| 37 | + | + | + | + | + | + | + |
| 38 | + | + | + | + | + | + | + |
| 39 | + | + | + | + | + | + | + |
| 40 | + | + | + | + | + | + | + |
| 41 | + | + | + | + | + | + | + |
| 42 | + | + | + | + | + | + | + |
| 43 | + | + | + | + | + | + | + |
| 44 | + | + | + | + | + | + | + |
| 45 | + | + | + | + | + | + | + |
| 46 | + | + | + | + | + | + | + |
| 47 | + | + | + | + | + | + | + |
| 48 | + | + | + | + | + | + | + |
| 49 | + | + | + | + | + | + | + |
| 50 | + | + | + | + | + | + | + |
| 51 | + | + | + | + | + | + | + |
| 52 | + | + | + | + | + | + | + |
| 53 | + | + | + | + | + | + | + |
| 54 | + | + | + | + | + | + | + |
| 55 | + | + | + | + | + | + | + |
| 56 | + | + | + | + | + | + | + |
| 57 | + | + | + | + | + | + | + |
| 58 | + | + | + | + | + | + | + |
| 59 | + | + | + | + | + | + | + |
| 60 | + | + | + | + | + | + | + |
| 61 | + | + | + | + | + | + | + |
| 62 | + | + | + | + | + | + | + |
| 63 | + | + | + | + | + | + | + |
| 64 | + | + | + | + | + | + | + |
| 65 | + | + | + | + | + | + | + |
| 66 | did not grow | | | | | | |

TABLE 4-continued
DNA DOT BLOT SUMMARY
PROBES

| STRAIN | r102 | 1A | 2A | 3 | 4 | 5 | 6 |
|--------|------|----|----|----|----|----|----|
| 67 | + | + | + | + | + | + | + |
| 68 | | | contaminated | | | | |
| 69 | + | + | + | + | + | + | + |
| 70 | + | + | + | + | + | + | + |
| 71 | + | + | + | + | + | + | + |
| 72 | + | + | + | + | + | + | + |
| 73 | + | + | + | + | + | + | + |
| 74 | + | + | + | + | + | + | + |
| 75 | + | + | + | + | + | + | + |
| 76 | + | + | + | + | + | + | + |
| 77 | + | + | + | + | + | + | + |
| 78 | + | + | + | + | + | + | + |
| 79 | + | + | + | + | + | + | + |
| 80 | + | + | + | + | + | + | + |
| 81 | + | + | + | + | + | + | + |
| 82 | + | + | + | + | + | + | + |
| 83 | + | + | + | + | + | + | + |
| 84 | + | + | + | + | + | + | + |
| 85 | + | + | + | + | + | + | + |
| 86 | + | + | + | + | + | + | + |
| 87 | + | + | + | + | + | + | + |
| 88 | + | + | + | + | + | + | + |
| 89 | + | + | + | + | + | + | + |
| 90 | + | + | + | + | + | + | + |
| 91 | + | + | + | + | + | + | + |
| 92 | + | + | + | + | + | + | + |
| 93 | + | + | + | + | + | + | + |
| 94 | + | + | + | + | + | + | + |
| 95 | + | + | + | + | + | + | + |
| 96 | + | + | + | + | + | + | + |
| 97 | + | + | + | + | + | + | + |
| 98 | + | + | + | + | + | + | + |
| 99 | + | − | + | + | + | + | + |
| 100 | + | + | + | + | + | + | + |
| 101 | + | + | + | + | + | + | + |
| 102 | + | + | + | + | + | + | + |
| 103 | + | + | + | + | + | + | + |
| 104 | + | + | + | + | + | + | + |
| 105 | + | + | + | + | + | + | + |
| 106 | + | + | + | + | + | + | + |
| 107 | + | + | + | + | + | + | + |
| 108 | + | + | + | + | + | + | + |
| 109 | + | + | + | + | + | + | + |
| 110 | + | + | + | + | + | + | + |
| 111 | + | + | + | + | + | + | + |
| 112 | + | + | + | + | + | + | + |
| 113 | + | + | + | + | + | + | + |
| 114 | + | + | + | + | + | + | + |
| 115 | + | + | + | + | + | + | + |
| 116 | + | + | + | + | + | + | + |
| 117 | + | + | + | + | + | + | + |
| 118 | + | + | + | + | + | + | + |
| 119 | + | + | + | + | + | + | + |
| 120 | + | + | + | + | + | + | + |
| 121 | + | + | + | + | + | + | + |
| 122 | + | + | + | + | + | + | + |
| 123 | + | + | + | + | + | + | + |
| 124 | + | + | + | + | + | + | + |
| 125 | + | + | + | + | + | + | + |
| 126 | + | + | + | + | + | + | + |
| 127 | + | + | + | + | + | + | + |
| 128 | + | + | + | + | + | + | + |
| 129 | + | + | + | + | + | + | + |
| 130 | + | + | + | + | + | + | + |
| 131 | + | + | + | + | + | + | + |
| 132 | + | + | + | + | + | + | + |
| 133 | + | + | + | + | + | + | + |
| 134 | + | + | + | + | + | + | + |
| 135 | + | + | + | + | + | + | + |
| 136 | + | + | + | + | + | + | + |
| 137 | + | + | + | + | + | + | + |
| 138 | + | + | + | + | + | + | + |
| 139 | | | did not grow | | | | |
| 140 | + | + | + | + | + | + | + |
| 141 | + | + | + | + | + | + | + |
| 142 | + | + | + | + | + | + | + |
| 143 | + | + | + | + | + | + | + |
| 144 | + | + | + | + | + | + | + |
| 145 | + | + | + | + | + | + | + |
| 146 | + | + | + | + | + | + | + |
| 147 | + | + | + | + | + | + | + |
| 148 | + | + | + | + | + | + | + |
| 149 | + | + | + | + | + | + | + |
| 150 | + | + | + | + | + | + | + |
| 151 | + | + | + | + | + | + | + |
| 152 | + | + | + | + | + | + | + |
| 153 | + | + | + | + | + | + | + |
| 154 | + | + | + | + | + | + | + |
| 155 | + | + | + | + | + | + | + |
| 156 | + | + | + | + | + | + | + |
| 157 | + | + | + | + | + | + | + |
| 158 | + | + | + | + | + | + | + |
| 159 | + | + | + | + | + | + | + |
| 160 | + | + | + | + | + | + | + |
| 161 | + | + | + | + | + | + | + |
| 162 | + | + | + | + | + | + | + |
| 163 | + | + | + | + | + | + | + |
| 164 | + | + | + | + | + | + | + |
| 165 | + | + | + | + | + | + | + |
| 166 | + | + | + | + | + | + | + |
| 167 | + | + | + | + | + | + | + |
| 168 | + | + | + | + | + | + | + |
| 169 | − | − | − | − | − | − | − |
| 170 | + | + | + | + | + | + | + |
| 171 | + | + | + | + | + | + | + |
| 172 | + | + | + | + | + | + | + |
| 173 | + | + | + | + | + | + | + |
| 174 | + | + | + | + | + | + | + |
| 175 | + | + | + | + | + | + | + |
| 176 | + | + | + | + | + | + | + |
| 177 | + | + | + | + | + | + | + |
| 178 | + | + | + | + | + | + | + |
| 179 | + | + | + | + | + | + | + |
| 180 | + | − | + | + | + | + | + |
| 181 | + | + | + | + | + | + | + |
| 182 | + | + | + | + | + | + | + |
| 183 | + | + | + | + | + | + | + |
| 184 | + | + | + | + | + | + | + |
| 185 | + | + | + | + | + | + | + |
| 186 | + | + | + | + | + | + | + |
| 187 | + | + | + | + | + | + | + |
| 188 | + | + | + | + | + | + | + |
| 189 | + | + | + | + | + | + | + |
| 190 | + | + | + | + | + | + | + |
| 191 | + | + | + | + | + | + | + |
| 192 | + | + | + | + | + | + | + |
| 193 | + | + | + | + | + | + | + |
| 194 | + | + | + | + | + | + | + |
| 195 | + | + | + | + | + | + | + |
| 196 | + | + | + | + | + | + | + |
| 197 | + | + | + | + | + | + | + |
| 198 | + | + | + | + | + | + | + |
| 199 | + | + | + | + | + | + | + |
| 200 | + | + | − | − | − | − | + |
| 201 | + | + | + | + | + | + | + |
| 202 | + | + | + | + | + | + | + |
| 203 | + | − | + | + | + | + | + |
| 204 | − | − | − | − | − | − | − |
| 205 | + | + | + | + | + | + | + |

Table 4, in its extensive testing and positive results, shows the usefulness of the system. The total efficiency of the probes is as follows:

| Probe | Positive Strains/Total | Efficiency |
|-------|------------------------|------------|
| 1A | 194/199 | 97.5 |
| 2A | 196/199 | 98.5 |
| 3 | 196/199 | 98.5 |
| 4 | 196/199 | 98.5 |
| 5 | 196/199 | 98.5 |
| 6 | 197/199 | 99.0 |

Example 17

In view of the results of Example 16, showing specificity for DNA, tests were carried out to test for RNA specificity. Twenty five strains were chosen at random, and RNA was extracted, either using standard methodologies or the methodology presented supra. Control strains were also used. Extracted RNA was quantitated and electrophoresed on 1% formaldehyde-agarose gels to check purity and integrity, after which 10 ug samples were applied to nylon membranes. The RNA was denatured by adding deionized formamide and formaldehyde, incubated at 50° C. for one hour, chilled on ice and then applied to membrane. Hybridization was carried out using 5' $^{32}$P end labelled probe overnight at 60° C., following the protocols set forth supra.

Probes 2A, 4 and 6 hybridized to the single stranded 16S rRNA whereas 1A, 3 and 5, which should be identical to the 16S rRNA, did not. The sensitivity in all three cases was 100%.

Discussion

The preceding examples describe an improved form of the strand displacement assay. Essentially, the method involves contacting a sample of interest with a hybrid complex. The complex contains a binding probe, and a signal probe. The first member of the complex may be divided into an initial binding region or "IBR", and target binding region. The target binding region and signal probe are hybridized to each other, and the IBR extends out from the complex. The whole of the binding probe must be complementary to the nucleic acid molecule to be assayed. The complex is added to the sample and the binding probe begins to hybridize to the nucleic acid analyte of the sample. Hybrids of longer sequences are more stable than shorter ones, so hybridization between target and probe is favored, leading to displacement to the signal probe. Once displaced, the signal probe is measured or observed, thereby providing a determination of the target analyte.

There are certain requirements on the members of the hybrid complex. With respect to the binding probe, the IBR must not be too long, so as to prevent hybridization to a non analyte sequence. This can happen with a binding probe if, for example, the IBR is 95% homologous to a non target sequence, and the 5% of difference is dispersed along the length of the IBR. When this happens, the IBR will, in effect, ignore the random areas of non-complementarity and hybridize anyway. To avoid such problems, the IBR must be short enough to prevent non-complementary binding. Similarly, the entire probe sequence must be short enough to prevent formation of stable hybrids with non complementary sequences. This can happen with a long probe even if the IBR does not engage in false hybridization, because the longer region will still hybridize. Preferably, the entire probe sequence is only from 20 to 40 bases in length, a length of from 25 to 35 bases being particularly preferred. Within these probe sequences, it is especially preferred if the IBR is 10 or fewer bases in length, thus leaving a target binding region that is preferably 10 to 30 or even 15 to 35 nucleotide bases in length. Especially good results were found, e.g., with base lengths of 7 bases for the IBR, and 25 bases for the target binding region.

Hybrid complexes of the type described herein are useful for determining analytes, and can discriminate down to the level of a single base pair difference. As such, the complexes are useful in diagnostic assays for diverse analytes and pathological conditions, including point mutations. Among the various diagnostic applications of the method are the determination of sexually transmitted diseases, virus infections, bacteria, chromosomal disorders, genetically inherited diseases, nucleic acid mutations, and so forth.

In carrying out the assays of the invention, as has been seen, solution and solid phase assays may both be carried out, the latter category being particularly preferred. Among the variations in the latter category are assays where the hybrid complex is bound to a solid such as a bead or a nitrocellulose paper or nylon membrane, and the signal probe is displaced therefrom. The displaced signal may then be measured. In such systems, the binding probe may be bound to the solid phase in a number of ways known to the skilled artisan, as immobilization of nucleic acids to solid phases is somewhat routine. Especially preferred systems immobilize the binding probe via a (strept)avidin-biotin binding system, where the elements of the binding system may be interchanged. Additional linker molecules may be used to bind the probe to the solid phase.

It is also possible, as shown, supra, to carry out the displacement assay and then add the solid phase so as to remove the complexes from the solution in which the assay is run. One then determines the amount of signal either on the solid phase or in solution.

The signal probe is, of course, labelled to facilitate its identification. Radiolabels, such as $^{32}$P and $^{35}$S, etc. may be used, as may any of the many signals used to label nucleic acid sequences. Metal particles, such as gold sols, may be used, as may fluorescent, chemiluminescent, or other materials which present an "inherent" signal, such as colored microparticles. Other labels may also be used which are not inherently signal producers in that they require further treatment to be detected. Such materials include enzymes, such as the peroxidases and alkaline phosphatases, where a substrate for the enzyme is added to provide a signal, magnetic particles, antigenic or haptenic molecules, antibodies, and so forth, where a further reaction is required to indicate the signal's presence.

The invention also includes reagent kits and complexes useful in carrying out displacement assays of the type described herein. The inventive complexes are those described supra. Reagent kits include the complex, and may include, e.g., a solid phase component for subsequent binding of the complex either before or after running the assay, and a signal means for detecting the label on the signal probe. The signal means is kept separate from the labeled sequence, while the solid phase material may or may not be directly bound to the binding probe. It is also possible, if desired, to present the binding probe and signal probe in separate portions of the kit.

The attachment of the complex to solid phases also allows the artisan to prepare diagnostic apparatus, where a solid carrier support, such as a nitrocellulose paper strip, has complex immobilized thereon. The strip may include at a point downstream of the attached complex a signal generating system for determining displaced label. The signal generating system may also be presented "off board" of the strip in the form, e.g., of a container of reagent.

The first few examples of this application also set forth isolated nucleic acid sequence which are useful as specific *N. gonorrhoea* diagnostic probes. These oligomers do not hybridize with other species of Neisseria to a degree leading to false positives, thereby making them especially useful in diagnosing gonorrhea. SEQ ID NOS: 1, 4–6, and 7, e.g., are examples of such oligomers. These probes may be labelled in any of the ways described supra, as well as all other ways known to the art. Different assay formats can be used in conjunction with the strand displacement assay as described. One particularly desirable application of the assay is in an automated system. In such a system, hybrid complex is immobilized on a solid phase, such as the inner wall of a test tube or reaction cuvette. The complex can be immobilized directly, via a (strept)avidin-biotin complex, or any of the other means available to the artisan for immobilization of nucleic acids. Sample is then added to the carrier of the complex, resulting in displacement of signal probe to sample liquid, supernatant, etc. The signal probe containing liquid may then be transferred to some point within the automated system where it is measured. Other aspects of the invention will also be clear to the skilled artisan, and need not be repeated here.

It will be understood that the specification and examples are illustrative but not limitative of the present invention and that other embodiments within the spirit and scope of the invention will suggest themselves to those skilled in the art.

We claim:

1. Method for determining presence of *Neisseria gonorrhea* in a sample, by detecting a target nucleotide sequence which is unique to *Neisseria gonorrhea* comprising: contacting said sample with a complex of
   (a) a probe nucleotide sequence selected from the group consisting of SEQ ID NO: 4, the sequence complementary to SEQ ID NO:4, SEQ ID NO: 5, the sequence complementary to SEQ ID NO: 5, SEQ ID NO: 6, and the sequence complementary to SEQ ID NO: 6 said probe nucleotide sequence comprising a target binding region and
   (b) a labelled nucleotide sequence, wherein said labelled nucleotide sequence is hybridized to at least a portion of said target binding region,
   wherein said target nucleotide sequence unique to *Neisseria gonorrhea* binds to said probe nucleotide sequence to displace said labelled nucleotide sequence therefrom, and
   (c) wherein the presence of displaced labelled nucleotide sequence in said sample is indicative of *Neisseria gonorrhea* in said sample.

2. The method of claim 1, wherein said method is carried out in solution.

3. The method of claim 1, wherein said method is carried out on a solid phase.

4. The method of claim 1, wherein said labelled nucleotide sequence is non-radioactively labelled.

5. The method of claim 1, wherein said labelled nucleotide sequence is labelled with a hapten.

6. The method of claim 5, wherein said hapten is biotin, fluorescein or digoxigenin.

7. Complex of nucleic acid molecules useful in determining *Neisseria gonorrhea* in a sample, consisting essentially of:
   (a) a probe selected from the group consisting of SEQ ID NO: 4, the sequence complementary to SEQ ID NO: 4, SEQ ID NO: 5, the sequence complementary to SEQ ID NO: 5, SEQ ID NO: 6, and the sequence complementary to SEQ ID NO: 6 and
   (b) a labelled nucleotide sequence hybridized to said probe along a portion of said probe.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

AGCCGCGAGG CGGAGCCA                                                                                                 1 8

( 2 ) INFORMATION FOR SEQ ID NO: 2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

AGCCGCGGCG GAGCCA                                                                                                   1 6

( 2 ) INFORMATION FOR SEQ ID NO: 3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AGCCGCGACG ATGCAT                                                                                               1 6

( 2 ) INFORMATION FOR SEQ ID NO: 4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

ACACGTGGAA TTCCACCTCC CTCTGAC                                                                     2 7

( 2 ) INFORMATION FOR SEQ ID NO: 5:

( i ) SEQUENCE CHARACTERISTICS:
        ( A ) LENGTH: 27 base pairs
        ( B ) TYPE: nucleic acid ( C ) STRANDEDNESS: single
( D ) TOPOLOGY: linear ( x i ) SEQUENCE DESCRIPTION: SEQ ID NO: 5:

CCCACGCTTT CGGACATGAA CGTCAGT     27

( 2 ) INFORMATION FOR SEQ ID NO: 6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

AGAGTGCCCA AACCGAATGA TGGCAAC     27

( 2 ) INFORMATION FOR SEQ ID NO: 7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GAGGCGGAGC CAATCTCACA AAACC     25

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

GAAGTCTGCC GTTACTG     17

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

CAGTAACGGC AGACTTCTCC TCAG     24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

CAGTAACGGC AGACTTCTCC ACAG     24

( 2 ) INFORMATION FOR SEQ ID NO:11:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

```
CTGACACAAC TGTGTTCACT AGCAACTTCA AACAGACACC ATGGTGCACC TGACTCCTGA       60

GGAGAAGTCT GCCGTTACTG                                                  80
```

( 2 ) INFORMATION FOR SEQ ID NO:12:

( i ) SEQUENCE CHARACTERISTICS:
  ( A ) LENGTH: 80 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 12:

```
CTGACACAAC TGTGTTCACT AGCAACTTCA AACAGACACC ATGGTGCACC TGACTCCTGT       60

GGAGAAGTCT GCCGTTACTG                                                  80
```